US00PP10139P

United States Patent [19]

Trees

[11] Patent Number: Plant 10,139

[45] Date of Patent: Dec. 2, 1997

[54] GERANIUM PLANT NAMED SUNRISE

[75] Inventor: Scott C. Trees, Arroyo Grande, Calif.

[73] Assignee: Ball Horticultural Company, West Chicago, Ill.

[21] Appl. No.: 701,181

[22] Filed: Aug. 21, 1996

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Burns, Doane, Swecker & Mathis, L.L.P.

[57] ABSTRACT

The new and distinct *Pelargonium×hortorum×Pelargonium×peltatum* cultivar of the ivy type named 'Sunrise' is provided. This new ivy/Zonal Geranium was the result of a controlled breeding program wherein a plant designated 1497-1 (non-patented in the United States) was pollinated by the 'Renee' cultivar U.S. Plant Pat. No. 7,353). The new cultivar forms attractive single coral red florets. The medium green foliage with slight zonation is well retained during shipment. The growth habit is medium vigorous and cascading with excellent basal branching in the absence of a growth regulator.

1 Drawing Sheet

SUMMARY OF THE INVENTION

The present invention comprises a new and distinct Geranium cultivar, botanically known as *Pelargonium×hortorum×Pelargonium×peltatum*, and hereinafter is referred to by the cultivar name 'Sunrise'.

The new cultivar is a product of a planned breeding program which had the objective of the creation of a new Geranium cultivar that exhibits uniform large round umbels, medium green foliage, excellent basal branching that requires no growth regulator, and a cascading growth habit.

The breeding program that resulted in the production of the new cultivar of the present invention was carried out in a controlled environment during 1991 at Arroyo Grande, Calif., U.S.A. The female parent (i.e., seed parent) was a plant designated 1497-1 (non-patented in the United States) which exhibits semi-double scarlet florets with dark green foliage. The male parent (i.e., pollen parent) was the 'Renee' cultivar U.S. Plant Pat. No. 7,353) which exhibits red florets with medium green ivy foliage. The parentage of the new 'Sunrise' cultivar can be summarized as follows:

1497-1×'Renee'.

'Sunrise' was discovered and selected during 1991 as a highly distinctive flowering plant from among the progeny of the stated cross at Arroyo Grande, Calif., U.S.A. This plant was initially designated BFP-919.

It was found that the new cultivar of the present invention:

(a) exhibits attractive single coral red florets,
(b) forms attractive medium green foliage with slight zonation, and
(c) exhibits a medium vigorous and cascading growth habit with excellent basal branching in the absence of a growth regulator.

The first act of asexual reproduction of the 'Sunrise' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1992 has demonstrated that the combination of unique characteristics as herein described for the 'Sunrise' cultivar is fixed and is retained through successive generations of such asexual reproduction.

The new 'Sunrise' cultivar has not been observed under all possible environmental conditions. Accordingly, the described phenotype may vary somewhat with variations in the environment, such as temperature, light intensity, and day length.

'Sunrise' is believed to be the only true coral red Zonal Geranium of the ivy type and can be readily distinguished by its cascading growth habit and large round umbels in combination with the flower coloration.

The new cultivar of the present invention is being marketed under the GALLERIA trademark.

BRIEF DESCRIPTION OF THE PHOTOGRAPH

The accompanying photograph shows the new 'Sunrise' cultivar with colors being as nearly true as it is reasonably possible to make the same in a color illustration of this character. The plant was being grown in a greenhouse at West Chicago, Ill., U.S.A. The general appearance of the overall plant including the flower and foliage characteristics is illustrated.

DETAILED DESCRIPTION

The following observations, measurements and comparisons describe plants grown in Ball FloraPlant's greenhouses located at West Chicago, Ill. U.S.A., under conditions which approximate those generally used in commercial practice. In the following description, color references are made to the R.H.S. Colour Chart of The Royal Horticultural Society, London, England. The color values were determined on September 22nd, under natural light conditions of 200 footcandles.

Classification:

*Botanical.*—*Pelargonium×hortorum×Pelargonium×peltatum*, cv. 'Sunrise'.

*Commercial.*—Ivy Zonal Geranium.

Inflorescence

A. Umbel:

*Average diameter.*—Approximately 8.4 to 9.4 cm.

*Average depth.*—Approximately 5 to 6 cm.

*Peduncle length.*—Approximately 9.5 to 12 cm.

*Pedicel length.*—Approximately 3.1 cm.

*Number of umbels/plant.*—When grown in a 10 cm. pot at 9 weeks after the sticking of a rooted cutting, there commonly are approximately 2 to 4 umbels per plant.

*Number of florets/umbel.*—When grown in 10 cm. pots at 9 weeks, approximately 16 to 19 florets per umbel commonly are formed.

B. Corolla:

*Average Diameter.*—Approximately 4.5 to 5.5 cm.

*Form.*—Single with an occasional petaloid.

*Color.*—General tonality from a distance of three meters: Coral red. Adaxial: Red Group 43B with the bases of the upper two petals being Red-Purple Group 64C and the veins being Red-Purple Group 59A. Abaxial: Red Group 43C.

Reproductive Organs:

*Androecium.*—The anthers are commonly approximately 3 mm. in length. The pollen color is Orange Group 28A. The filaments are approximately 6 to 7 min. in length.

*Gynoecium.*—The pistil length commonly is approximately 11 mm. There is a single stigma which commonly has a length of approximately 4 mm. which commonly branches into 5 parts, the ovary is approximately 2 mm. in length, and the style length is approximately 5 min.

*Fertility.*—Commonly does not produce fruits in the absence of mechanical fertilization.

D. Spring flowering response period: Approximately 6 to 7 weeks from rooted cuttings under greenhouse conditions.

E. Outdoor flower production: Freely flowering under outdoor growing conditions with substantially continuous blooming.

F. Durability: Ships well.

Plant

A. Foliage: Medium green.

*Form.*—Reniform, with a cordate base.

*Margin.*—Crenate.

*Color.*—Adaxial: Yellow-Green Group 146A at the outer edges and slightly lighter than Yellow-Green Group 146A towards the center. Abaxial: Yellow-Green Group 147C.

*Size.*—Approximately 8.5 cm. at the widest point and approximately 7.5 cm. at the narrowest point.

B. General appearance and form:

*Internode length.*—*Commonly varies from approximately* 1.5 to 3 cm.

*Branching pattern.*—Freely basal branching. No pinching is required to obtain self-branching. A medium vigorous and cascading growth habit with excellent branching is observed in the absence of a growth regulator.

*Height.*—Approximately 18 to 24 cm. above a 10 cm. pot at 9 weeks under standard greenhouse conditions.

I claim:

1. A new and distinct variety of Geranium plant named 'Sunrise', substantially as herein shown and described, which:

(a) exhibits attractive single coral red florets, (b) forms attractive medium green foliage with slight zonation, and (c) exhibits a medium vigorous and cascading growth habit with excellent basal branching in the absence of a growth regulator.

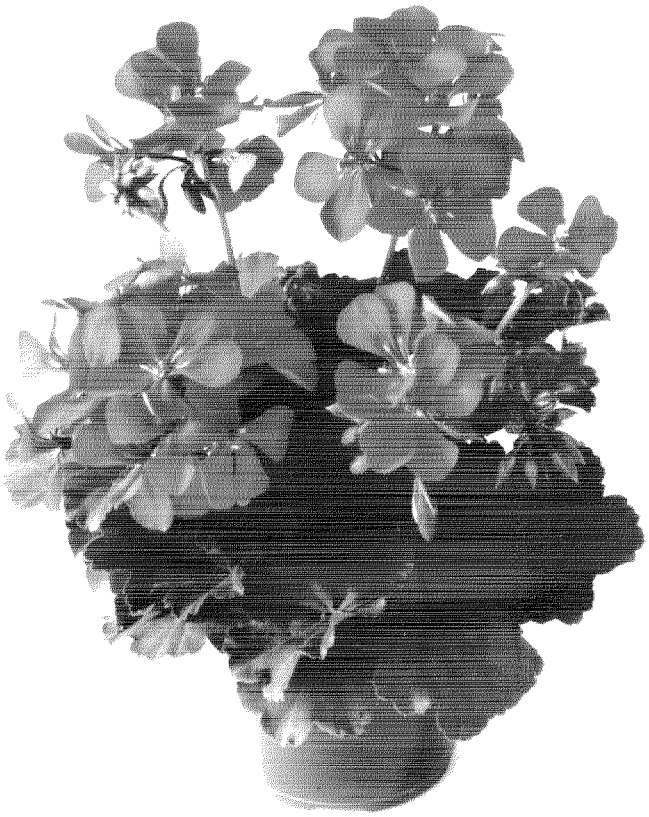

* * * * *